(12) United States Patent
Vaughan et al.

(10) Patent No.: US 11,242,470 B2
(45) Date of Patent: Feb. 8, 2022

(54) HOT MELT ADHESIVE WITH HIGH SOFTENING POINT TACKIFYING AGENT

(71) Applicant: H.B. Fuller Company, St. Paul, MN (US)

(72) Inventors: Steven R. Vaughan, Lake Elmo, MN (US); Kevin P. Davis, Woodbury, MN (US); Thomas Wittkopf, Vogelsen (DE); Peter Remmers, Hamburg (DE); Seth Urtel, Blaine, MN (US)

(73) Assignee: H.B. Fuller Company, St. Paul, MN (US)

( * ) Notice: Subject to any disclaimer, the term of this patent is extended or adjusted under 35 U.S.C. 154(b) by 276 days.

(21) Appl. No.: 16/206,300

(22) Filed: Nov. 30, 2018

(65) Prior Publication Data
US 2019/0161649 A1 May 30, 2019

Related U.S. Application Data

(60) Provisional application No. 62/592,606, filed on Nov. 30, 2017.

(51) Int. Cl.
| | |
|---|---|
| *C09J 7/35* | (2018.01) |
| *C09J 123/12* | (2006.01) |
| *C09J 11/08* | (2006.01) |
| *C09J 11/06* | (2006.01) |
| *A61F 13/539* | (2006.01) |
| *C09J 123/14* | (2006.01) |
| *A61F 13/537* | (2006.01) |
| *A61F 13/15* | (2006.01) |

(52) U.S. Cl.
CPC ............... *C09J 7/35* (2018.01); *A61F 13/539* (2013.01); *A61F 13/53747* (2013.01); *C09J 11/06* (2013.01); *C09J 11/08* (2013.01); *C09J 123/12* (2013.01); *C09J 123/14* (2013.01); *A61F 13/15585* (2013.01); *A61F 2013/53908* (2013.01)

(58) Field of Classification Search
CPC ..... C09J 7/35; C09J 11/06; C09J 11/08; C09J 123/12; A61F 13/539; A61F 2013/53908
See application file for complete search history.

(56) References Cited

U.S. PATENT DOCUMENTS

| | | | |
|---|---|---|---|
| 4,217,428 A | 8/1980 | McConnell et al. | |
| 4,572,874 A | 2/1986 | Chang et al. | |
| 4,886,853 A | 12/1989 | Foster et al. | |
| 6,008,148 A | 12/1999 | Harris et al. | |
| 7,199,180 B1 | 4/2007 | Simmons et al. | |
| 8,921,474 B2 | 12/2014 | Alper et al. | |
| 9,115,299 B2 | 8/2015 | Hu et al. | |
| 9,522,213 B2 | 12/2016 | Davis et al. | |
| 2004/0059018 A1* | 3/2004 | Gagliardi | A61F 13/53 523/111 |
| 2007/0135563 A1* | 6/2007 | Simmons | C08L 23/04 524/570 |
| 2012/0329353 A1 | 12/2012 | Davis et al. | |
| 2013/0202902 A1 | 8/2013 | Dejesus et al. | |
| 2014/0350155 A1* | 11/2014 | Hamann | C08L 91/06 524/226 |
| 2015/0024649 A1 | 1/2015 | Czaplewski et al. | |
| 2015/0299526 A1 | 10/2015 | Gray et al. | |
| 2016/0102230 A1 | 4/2016 | Gray et al. | |
| 2016/0121014 A1 | 5/2016 | Remmers et al. | |
| 2017/0290245 P1 | 10/2017 | Hanson et al. | |

FOREIGN PATENT DOCUMENTS

| | | |
|---|---|---|
| EP | 1208181 | 10/2004 |
| WO | WO2014204944 | 12/2014 |
| WO | WO2016140830 | 9/2016 |
| WO | WO2016153663 | 9/2016 |
| WO | WO2017177164 | 10/2017 |
| WO | WO2018027055 | 2/2018 |

* cited by examiner

*Primary Examiner* — Jeremy R Pierce
(74) *Attorney, Agent, or Firm* — Kirsten Stone; Kristi Halloran

(57) ABSTRACT

The invention includes a hot melt adhesive composition including an olefin polymer and a high melt point hydrocarbon tackifying agent, such compositions unexpectedly provide improved bonding between the layers found in a disposable absorbent article. In particular, such compositions improve the bond between the nonwoven top sheet and the acquisition distribution layer.

11 Claims, No Drawings

HOT MELT ADHESIVE WITH HIGH SOFTENING POINT TACKIFYING AGENT

This application claims the benefit of U.S. Provisional Application No. 62/592,606 filed Nov. 30, 2017, which is incorporated herein.

BACKGROUND

Adhesives are often used to bond substrates together so as to maintain the two substrates in a fixed relation to each other. In the area of industrial adhesives, hot melt adhesives are commonly used to bond together a wide variety of articles including disposable absorbent articles comprising non-woven substrates e.g. adult incontinence products, disposable diapers, sanitary napkins, bed pads, puppy pads, medical dressings, etc.

There can be multiple hot melt adhesives used in the manufacture of a disposable absorbent article. For example, in the manufacture of a disposable diaper, hot melt adhesives are used in construction (e.g. bonding the back sheet to the nonwoven and optionally the absorbent pad), elastic attachment (e.g. bonding the elastic material to the back sheet in for example the leg or waist area), and for core stabilization (e.g. applying an adhesive to the absorbent core to increase the strength of the core).

Hot melt adhesives can also be used to bond sub layers together within the disposable article. In particular, hot melt adhesives can be used to bond the top sheet to the acquisition distribution layer (ADL) or transfer layer. The acquisition distribution layer is a sub-layer immediately above the core that is designed to improve fluid distribution in disposable articles. ADL layers have excellent hydrophilic properties and can be difficult to bond to with olefin polymer containing hot melt adhesives.

SUMMARY

In one aspect, the invention features a disposable absorbent article including a top sheet, an acquisition distribution layer, and a hot melt adhesive composition including an olefin polymer, and from 5% by weight to 60% by weight of a high softening point hydrocarbon tackifying agent having a softening point of from 110° C. to 150° C., wherein the hot melt adhesive composition adheres the top sheet to the acquisition distribution layer.

In one embodiment, the hot melt adhesive composition further comprises from 3% by weight to 35% by weight of a plasticizer. In another embodiment, the high softening point hydrocarbon tackifying agent is present at from 20% by weight to 55% by weight.

In a different embodiment, high softening point hydrocarbon tackifying agent is selected from the group consisting of aliphatic and cycloaliphatic hydrocarbon resins. In one embodiment, the high softening point hydrocarbon tackifying agent has an aromatic content as tested by Nuclear Magnetic Resonance (NMR) of from 0% by weight to 20% by weight in some embodiments, the high softening point hydrocarbon tackifying agent is at least partially hydrogenated. In another embodiment, the high softening point hydrocarbon tackifying agent has a softening point of from 115° C. to 145° C.

In one embodiment, the olefin polymer is a single site catalyzed propylene based polymer. In a different embodiment, the olefin polymer is a single site catalyzed propylene based polymer and the hydrocarbon tackifying agent is present at from 30% by weight to 40% by weight.

In some embodiments, the acquisition distribution layer is a hydrophilic nonwoven.

In another embodiment, the disposable absorbent article is selected from the group consisting of a disposable diaper and an adult incontinence product.

In one aspect, the invention features a hot melt adhesive composition including from 22% by weight to 55% by weight of a single site catalyzed propylene based polymer that has a co-monomer content of from 0% by weight to 20% by weight and a Brookfield Viscosity at 190° C. of no greater than 25,000, from 25% by weight to 55% by weight of a high softening point hydrocarbon tackifying agent, that is at least partially hydrogenated, having a softening point of from around 110° C. to around 150° C., and from 3% by weight to 35% by weight of plasticizer.

In one embodiment, the high softening point hydrocarbon tackifying agent is present at from 30% by weight to 45% by weight. In another embodiment, the high softening point hydrocarbon tackifying agent has an aromatic content as tested by Nuclear Magnetic Resonance (NMR) of from 0% by weight to 20% by weight. In some embodiments, the hot melt adhesive composition further comprises a second tackifying agent.

In a different embodiment, the hot melt adhesive further includes less than 10% by weight a propylene based polymer having a melt index (190° C., 2.16 kg), tested according to ASTM D1238 of from 1 to 30. In one embodiment, the hot melt adhesive further includes a wax. In some embodiments, the total amount of propylene-based polymer is present at from 35% to 50% by weight.

In one embodiment, the hot melt adhesive composition has a Brookfield Viscosity at 150° C. of no greater than 16,000 cP. In another embodiment the invention includes a disposable absorbent article including a hydrophilic substrate bonded with the hot melt adhesive composition.

Applicants have found that hot melt adhesive compositions including an olefin polymer and a high melt point hydrocarbon tackifying agent unexpectedly provide improved bonding between the layers found in a disposable absorbent article. Specifically, such compositions give an improved bond to hydrophilic nonwoven substrates (e.g. improving the bond between the nonwoven top sheet and the acquisition distribution layer).

Glossary

In reference to the invention, these terms have the meanings set forth below:

Ethylene-based refers to a polymer that comprises at least 50% by weight ethylene.

Propylene-based refers to a polymer that comprises at least 50% by weight propylene.

Butene-based refers to a polymer that comprises at least 50% by weight butene.

DETAILED DESCRIPTION

Disposable Absorbent Article

The invention includes a disposable absorbent article including a hydrophilic substrate bonded with a hot melt adhesive including an olefin polymer and from 5% by weight to 60% by weight of a high softening point hydrocarbon tackifying agent having a softening point of from 110° C. to 150° C.

The invention further includes a disposable absorbent article including a top sheet, an acquisition distribution layer, and a hot melt adhesive including an olefin polymer and from 5% by weight to 60% by weight of a high softening point hydrocarbon tackifying agent with a softening point of from 110° C. to 150° C., wherein the hot melt adhesive composition adheres the top sheet to the acquisition distribution layer.

Top Sheet

The top sheet is liquid-permeable and makes up the body facing layer of the disposable absorbent article.

The top sheet may be constructed from a wide range of suitable materials including apertured films, nonwoven webs of natural fibers (e.g., wood or cotton) or synthetic fibers (e.g., polypropylene or polyester) or a combination of such fibers. The top sheet can include high loft materials or multiple layers of materials. High loft is a general term for low density, thick or bulky materials, as compared to flat, paper like materials. It is characterized by a relatively high ratio of thickness to weight per unit area. The top sheet can be hydrophobic or hydrophilic (e.g. surfactant treated). The top sheet can be hydrophobic, with the exception of the area in the center which can be treated with surfactant to be hydrophilic.

Acquisition Distribution Layer

The Acquisition Distribution Layer (ADL) or Transfer Layer s a sub-layer located beneath the top sheet designed to improve fluid distribution into the core in a disposable absorbent article. The ADL can be a hydrophilic nonwoven. A hydrophilic nonwoven has an affinity to water. This affinity can be achieved by using a nonwoven comprising hydrophilic fibers. Alternatively, a hydrophobic nonwoven can be treated with a chemical (e.g. surfactant, wetting agent, etc.) to improve its affinity to water. The ADL can be a high loft non-woven.

Hot Melt Adhesive Composition

The hot melt adhesive composition can be a pressure sensitive adhesive. The hot melt adhesive composition can have an Initial Gardner Color after manufacturing of less than 3, or even less than 2. The hot melt adhesive composition can have low odor.

The hot melt adhesive composition includes an olefin polymer and from 5% by weight 60% by weight of a high softening point hydrocarbon tackifying agent having a softening point of from 110° C. to 150° C.

The olefin polymer, the high softening point tackifying agent, the second tackifying agent and the plasticizer can make up at least 85% of the composition, at least 90% of the composition, or even at least 93% of the composition.

The viscosity of the hot melt adhesive composition can be no greater than 20,000 cP at 150° C., no greater than 16,000 cP at 150° C., no greater than 12,000 cP at 150° C., no greater than 10,000 cP at 150° C., from 2,000 cP to 20,000 cP at 150° C., or even from 500 cP to 15,000 cP at 150° C.

Olefin Polymer

The olefin polymer can be selected from a group consisting of ethylene based, propylene based and butene based olefin polymers.

The olefin polymer can be made using any type of catalyst system. In a preferred embodiment, the olefin polymer can be selected from the group consisting of single-site (e.g. metallocene) catalyzed and Ziegler Natta catalyzed polymers.

The olefin polymer can have a Brookfield Viscosity at 190° C. of no greater than 25,000 cP, no greater than 20,000 cP, no greater than 15,000 cP, from 500 cP to 25,000 cP, from 2500 cP to 15,000 cP, or even from 3,000 cP to 12,000 cP.

Alternatively, the olefin polymer can have a melt index (190° C., 2.16 kg), tested according to ASTM D1238 of less than 30, from 1 to 30, from 2 to 25, or even from 2 to 15.

The hot melt adhesive composition can include less than 15% by weight, less than 10% by weight, less than 8% by weight, from 2% to 15%, or even from 2% to 9% by weight of an olefin polymer having a melt index (190° C., 2.16 kg), tested according to ASTM D1238 of from 1 to 30.

The olefin polymer can be a blend of two of more olefin polymers. In one embodiment, the olefin polymer includes at least two olefin polymers, one having a Brookfield Viscosity at 190° C. of no greater than 25,000 cP and a second having a melt index (190° C., 2.16 kg), tested according to ASTM D1238 of from 1 to 30.

In another embodiment, the olefin polymer includes at least two olefin polymers, one having a Brookfield Viscosity at 190° C. of from 100 cP to 25,000 cP and a second having a melt index (190° C., 2.16 kg), tested according to ASTM D1238 of from 1 to 30.

In one embodiment, the olefin polymer has a limited amount of crystallinity.

The olefin polymer can have a Heat of fusion ($\Delta H$) as determined using differential scanning calorimetry according to ASTM E-793-06 entitled, "Standard Test Method for Enthalpies of Fusion and Crystallization by Differential Scanning calorimetry" of from 10 to 50 joules/gram, or even from 15 to 40 joules/gram.

The olefin polymer is present at from 10% by weight to 80% by weight, from 15% by weight to 60% by weight, from 22% by weight to 55% by weight, from by weight to 50% by weight, from 35% by weight to 50% by weight, or even from greater than 40% by weight to 60% by weight.

The olefin polymer can be a single site catalyzed propylene based polymer. The single site catalyzed propylene based polymer can be copolymer or a homopolymer.

The single site catalyzed propylene copolymer can be derived from propylene and at least one alpha-olefin co-monomer other than propylene C2, and C4-C20 alpha-olefin co-monomers, and combinations thereof). Useful alpha-olefin co-monomers include, e.g., alpha-olefin monomers having at least two carbon atoms, at least four carbon atoms, from four carbon atoms to eight carbon atoms, and combinations thereof. Examples of suitable classes of alpha-olefin co-monomers include mono-alpha olefins (i.e., one unsaturated double bond) and higher order alpha olefins (e.g., dienes (e.g., 1,9-decadiene)). Suitable alpha-olefin monomers include, e.g., ethylene, butene, pentene, hexene, heptene, octene, nonene, decene, dodecene, 4-methyl-pentene-1,3-methyl pentene-1,3,5,5-trimethyl-hexene-1,5-ethyl-1-nonene, and combinations thereof. Specific examples of suitable propylene-alpha-olefin copolymers include propylene-ethylene, propylene-butene, propylene-hexene, propylene-octene, and combinations thereof.

The single site catalyzed propylene based polymer can have a co-monomer content of from 0% to 30%, from 5% by weight to 20% by weight, from 6% by weight to 15% by weight, or even from 7% to 12% by weight.

Useful commercially available olefin polymers include e.g., VISTAMAXX 8880, VISTAMAXX 8380, VISTAMAXX 8780 and VISTAMAXX 6202 all propylene ethylene copolymers from ExxonMobil Chemical Company (Houston, Tex.), LICOCENE 1602 and LICOCENE 2602 from Clariant International Ltd. (Muttenz, Switzerland), the LMODU series of trade designations from Idemitsu Kosan Co., Ltd. (Japan) including LMODU S400 and LMODU S410 propylene homopolymers, the AERAFIN series of trade designations from Eastman Chemical Company (Kingsport, Tenn.) including AERAFIN 17 and AERAFIN 180 propylene-ethylene copolymers and the AFFINITY series of trade designations from DowDuPont Chemical Company (Midland, Mich.) including, e.g., AFFINITY GA 1900, AFFINITY GA 1950, and AFFINITY EG 8200, ethylene-octene copolymers, AFFINITY GP ethylene-propylene copolymers, and AFFINITY 1000R, a maleic anhydride modified ethylene-octene copolymer all available from DowDuPont Chemical Company (Midland, Mich.).

Plasticizer

The hot melt adhesive composition can include a plasticizer. Suitable plasticizers include, e.g., naphthenic oils, paraffinic oils (e.g., cycloparaffin oils), mineral oils, phthalate esters, adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil), derivatives of oils, glycerol esters of fatty acids, polyesters, polyethers, lactic acid derivatives and combinations thereof.

Useful commercially available plasticizers include CALSOL 5550, napthenic oil from Calumet Specialty Products Partners, LP (Indianapolis, Ind.), KAYDOL OIL, mineral oil from Sonneborn (Tarrytown N.Y.) PARAPOL polybutene from Exxon Mobil Chemical Company (Houston, Tex.), OPPANOL polyisobutylene from BASF (Ludwigsjhafen, Germany), KRYSTOL 550 mineral oil from Petrochem Carless Limited (Surrey, England) and PURETOL 35 mineral oil from Petro Canada Lubricants Inc. (Mississauga, Ontario).

In one embodiment, the plasticizer is a naphthenic oil.

The plasticizer is present in the hot melt adhesive composition at from 0% to 40%, at from 3% by weight to 35% by weight, from 10% by weight to 30% by weight, or even from 15% to 24% by weight.

High Softening Point Hydrocarbon Tackifying Agent

The hot melt adhesive composition includes a high softening point hydrocarbon tackifying agent with a softening point of from 110° C. to 150° C., from 115° C. to 145° C., from 113° C. to 145° C., or even from 120° C. to 135° C.

The high softening point hydrocarbon tackifying agent can be at least partially hydrogenated in order to improve the odor of the adhesive. Suitable classes of high melt point hydrocarbon tackifying agents include, e.g., aliphatic and cycloaliphatic hydrocarbon resins C9 and dicyclopentadiene (DCPD) based resins), mixed aromatic and aliphatic modified hydrocarbon resins, aromatic modified aliphatic hydrocarbon resins, and hydrogenated versions thereof; terpenes, modified terpenes and hydrogenated versions thereof.

The high softening point hydrocarbon tackifying agent is primarily aliphatic. The high softening point hydrocarbon tackifying agent can have an aliphatic content as tested by Nuclear Magnetic Resonance (NMR) of from 70% by weight to 100% by weight, or even from 80% by weight to 100% by weight.

If desired, the high softening point hydrocarbon tackifying agent can have limited aromatic content. The high softening point hydrocarbon tackifying agent can have an aromatic content as tested by Nuclear Magnetic Resonance (NMR) of from 0% by weight to 20% by weight, from 0% by weight to 15% by weight, or even from 0% by weight to 10% by weight.

The hot melt adhesive composition can include more than one high softening point hydrocarbon tackifying agent.

Useful high softening point hydrocarbon tackifying agents are commercially available under a variety of trade designations including, e.g., ESCOREZ 5637 from Exxon Mobil Chemical Company (Houston, Tex.), EASTOTAC H-115, H-130 and H-142 (grades L, R and W) from Eastman Chemical (Kingsport, Tenn.), RESINALL 81030 from Resinal Corp (Severn, N.C.), and SUKOREZ SU-110, SU-120, SU-130, SU-210, SU-230, SU-230S, SU-420, SU-525 from Kolon Industries, Inc. (Ulsan, Korea).

The high softening point hydrocarbon tackifying agent is present at from 5% by weight to 60% by weight, from 15% to 60%, from 20% to 55% by weight, from 25% by weight to 55% by weight, from 30% by weight to 50% by weight, from 30% by weight to 45% by weight, or even from 30% by weight to 40% by weight.

Second Tackifying Agent

The hot melt adhesive composition can include a second tackifying agent different from the high softening point hydrocarbon tackifying agent.

The second tackifying agent can be fluid or solid at room temperature. Suitable classes of second tackifying agents include, e.g., aromatic, aliphatic and cycloaliphatic hydrocarbon resins (including hydrocarbon tackifying agents with a lower softening point), mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof; low molecular weight polylactic acid; and combinations thereof. Examples of useful natural and modified rosins include gum rosin, wood rosin, tall oil rosin, distilled rosin, hydrogenated rosin, dimerized rosin and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin.

The hot melt adhesive composition can include from 5% by weight to 40% by weight, from 5% by weight to 30% by weight, or even from 10% by weight to 40% by weight of the second tackifying agent.

Wax

The hot melt adhesive composition can be free of a wax, alternatively the hot melt adhesive composition can include a wax. Useful classes of wax include, e.g., paraffin waxes, microcrystalline waxes, high density low molecular weight polyethylene waxes, by-product polyethylene waxes, polypropylene waxes, Fischer-Tropsch waxes, oxidized Fischer-Tropsch waxes, functionalized waxes such as acid, anhydride, and hydroxyl modified waxes, animal waxes, vegetable waxes (e.g. soy wax) and combinations thereof. Useful waxes are solid at room temperature and preferably have a Ring and Ball softening point of from 50° C. to 170° C. The wax can be a propylene based wax with a Mettler Softening Point (ASTM D 6092) of greater than 130° C., greater than 140° C., or even greater than 150° C. Useful waxes are commercially available from a variety of suppliers including polypropylene and polyethylene waxes available under the EPOLENE N and C series of trade designations from Westlake Chemical Corporation (Houston, Tex.) including e.g. EPOLENE N-21, EPOLENE N-15 and polypropylene and polyethylene waxes available under the LICOCENE series of trade designations from Clariant International Ltd. (Muttenz, Switzerland) including e.g. LICOCENE PP 6102, LICOCENE PP 6502 TP and LICOCENE PP 7502 TP.

The hot melt adhesive composition can include no greater than 10% by weight, no greater than 5% by weight, from 2% by weight to 10% by weight, or even from 3% to 8% by weight wax.

Additional Components

The hot melt adhesive composition optionally includes additional components including, e.g., stabilizers, antioxidants, additional polymers (e.g. styrenic block copolymers), adhesion promoters, ultraviolet light stabilizers, corrosion inhibitors, colorants (e.g., pigments and dyes), fillers, surfactants, wetness indicators, superabsorbents and combinations thereof.

Useful antioxidants include, pentaerythritol tetrakis[3,(3, 5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J.), and ETHYL 702 4,4'-methylene bis(2,6-di-tert-butylphenol). When present, the adhesive composition preferably includes from 0.1% by weight to 2% by weight antioxidant.

Disposable Absorbent Article

The hot melt adhesive composition can be used to bond to hydrophilic substrates.

The hot melt adhesive composition can be applied to (i.e. such that it is in direct contact with) the top sheet or the ADL and then a bond formed between the two.

The hot melt adhesive can further be incorporated in a variety of substrates within the disposable absorbent article including, e.g., films (e.g., polyolefin polyethylene and polypropylene) films), release liners, porous substrates, cellulose substrates, sheets (e.g., paper, and fiber sheets), paper products, woven and nonwoven webs, fibers (e.g., synthetic polymer fibers and cellulose fibers), elastics and tape backings.

The hot melt adhesive composition is also useful in a variety of applications and constructions including, e.g., disposable absorbent articles including, e.g., disposable diapers, adult incontinence products, sanitary napkins, medical dressings (e.g., wound care products), bandages, surgical pads, pet training pads (e.g. puppy pads) and meat-packing products, and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue).

The hot melt adhesive composition is useful on substrates made from a variety of fibers including, e.g., natural cellulose fibers such as wood pulp, cotton, silk and wool; synthetic fibers such as nylon, rayon, polyesters, acrylics, polypropylenes, polyethylene, polyvinyl chloride, polyurethane, and glass; recycled fibers, and various combinations thereof.

Various application techniques can be used to apply the hot melt adhesive composition to a substrate including, e.g., slot coating, spraying including, e.g., spiral spraying and random spraying, screen printing, foaming, engraved roller, extrusion and meltblown application techniques.

Methods of Making a Disposable Absorbent Article

The hot melt adhesive composition has good adhesion to hydrophilic substrates. This property makes it useful in bonding together various substrates found in disposable absorbent articles (e.g. bonding the ADL to the top sheet).

The hot melt adhesive composition can also be used for various construction applications. In a typical construction application in the manufacture of a disposable absorbent article, a body fluid impermeable backsheet is bonded to a nonwoven substrate. The adhesive may also be used to bond at least one additional layer or material selected from the group consisting of absorbents, tissues, elastomeric materials, superabsorbent polymers, and combinations thereof. For example, the adhesive can further be used for back sheet lamination i.e. where the body fluid impermeable backsheet typically a polyolefin film (e.g. polyethylene, polypropylene, ethylene vinyl acetate, ethylene copolymer, etc.) is bonded to a second nonwoven to improve the feel of the disposable article.

The invention will now be described by way of the following non-limiting examples. All parts, ratios, percents and amounts stated in the Examples are by weight unless otherwise specified.

EXAMPLES

Test Procedures

Test procedures used in the examples and throughout the specification, unless stated otherwise, include the following.

Sample Adhesive Sample Preparation

The hot melt adhesive samples were prepared in a sigma blade mixer with a batch size of 5000 grams. A heating oil temperature of around 177° C. was used. The polymer, tackifying agent and additives were added first, blended until smooth and then the plasticizer was added in portions. The mixture was allowed to mix until homogeneous and then dumped. Each sample took about 1 hour to make.

Tackifying Agent Softening Point

ASTM D 6090, with a heating rate of 1.4° C./min.

Viscosity Test Method

Viscosity is determined in accordance with ASTM D-3236 entitled, "Standard Test Method for Apparent viscosity of Adhesives and Coating Materials," (Oct. 31, 1988), using a Brookfield Thermosel viscometer Model RVDV 2 and a number 27 spindle. The results are reported in centipoise (cP).

T-Peel Test Sample Preparation

A slot coat applicator and laminator were set to an application temperature of 150° C., a nip pressure of 41.4 kilopascal (6 psi) and minimal rewind and unwind tensions so as not to stretch film. A continuous slot pattern of 7.6 centimeters (3.0 inches) wide was used. A top sheet nonwoven (UNIPRO 45 nonwoven web from Midwest Filtration Company), was passed through the applicator. A coat weight of 5 gsm (grams per meter squared) was applied to the top sheet nonwoven and then the nonwoven and adhesive were nipped to the ADL (MESA Carded Resin Bond) to form a laminate.

The speed at which the film passed through the applicator was from 213.4 meters per minute (700 feet per minute (ft/min)) to 274.3 meters per minute (900 ft/min). A sufficient amount of laminate was prepared such that 152.4 centimeters (60 inches) of representative lamination was be collected for testing.

T-Peel Test Method

The T-Peel test was used to measure the bond strength of the adhesive coated between two flexible substrates. T-Peel was determined using ASTM D1876-01 entitled, "Test Method for Determining Peel Resistance of Adhesive (T-Peel Test Method)," with the exception that it was run at 30.5 centimeters per minute (12 inches per minute), instead of 25.4 centimeters per minute (10 inches per minute), over a period of 10 seconds, and 7 replicates are run instead of the 10 specified in ASTM D1876. The samples were run on an INSTRON type test instrument. Unless otherwise specified, the test samples are prepared as described in the Sample Preparation. The average peel value over 10 seconds of peeling is recorded, and the results are reported in grams. The initial T-Peel value is the value measured 24 hours after the laminate is prepared.

TABLE 1

| | \multicolumn{8}{c}{Example} | | | | | | | |
|---|---|---|---|---|---|---|---|---|
| | C1 | Ex 1 | C2 | Ex2 | Ex 3 | Ex 4 | C3 | Ex 5 |
| AFFINITY EG8200 | 15 | 15 | | | | | | |
| LMODU400 | | | | | | | 40 | 40 |
| VISTAMAXX 8380 | | | 40 | 40 | 40 | 40 | | |
| EASTOTAC H100R (softening point = 100° C.) | 55 | | 37 | | | | 37 | |
| EASTOTAC H115R (softening point = 115° C.) | | | | 37 | | | | |
| EASTOTAC H130R (softening point = 130° C.) | | 55 | | | 37 | | | 37 |
| EASTOTAC H142 (softening point = 142° C.) | | | | | | 37 | | |
| CALSOL 5550 | 27 | 27 | 20 | 20 | 20 | 20 | 20 | 20 |
| EPOLENE C13 | 2 | 2 | 2 | 2 | 2 | 2 | 2 | 2 |
| IRGANOX 1076 | 1 | 1 | 1 | 1 | 1 | 1 | 1 | 1 |
| Substrate: TSNW/ADL | | | | | | | | |
| Peak Peel (Grams) | 72 | 90 | 5 | 39 | 41 | 62 | 24 | 47 |
| Average Peel (Grams) | 46 | 60 | 1 | 25 | 26 | 42 | 11 | 28 |

TSNW (Top Sheet Nonwoven - UNIPRO 45 nonwoven web from Midwest Filtration Company)
ADL (Acquisition Distribution Layer - Fitesa Carded Resin Bond (RB) is a multi-denier polyester resin bond fabric)

Other embodiments are within the claims.

What is claimed is:

1. A disposable absorbent article comprising:
   a top sheet,
   an acquisition distribution layer, and
   a hot melt adhesive composition comprising,
      an olefin polymer, and
      from 5% by weight to 60% by weight of a high softening point hydrocarbon tackifying agent having a softening point of from 110° C. to 150° C.,
   wherein the hot melt adhesive composition adheres the top sheet to the acquisition distribution layer, and the acquisition distribution layer is a hydrophilic substrate.

2. The disposable absorbent article of claim 1 wherein the hot melt adhesive composition further comprises from 3% by weight to 35% by weight of a plasticizer.

3. The disposable absorbent article of claim 1 wherein the hot melt adhesive composition comprises from 20% by weight to 55% by weight of the high softening point hydrocarbon tackifying agent.

4. The disposable absorbent article of claim 1 wherein the high softening point hydrocarbon tackifying agent is selected from the group consisting of aliphatic and cycloaliphatic hydrocarbon resins.

5. The disposable absorbent article of claim 1 wherein the high softening point hydrocarbon tackifying agent has an aromatic content as tested by Nuclear Magnetic Resonance (NMR) of from 0% by weight to 20% by weight.

6. The disposable absorbent article of claim 1 wherein the high softening point hydrocarbon tackifying agent is at least partially hydrogenated.

7. The disposable absorbent article of claim 1 wherein the high softening point hydrocarbon tackifying agent has a softening point of from 115° C. to 145° C.

8. The disposable absorbent article of claim 1 wherein the olefin polymer is a single site catalyzed propylene based polymer.

9. The disposable absorbent article of claim 1 wherein the olefin polymer is a single site catalyzed propylene based polymer and the hot melt adhesive composition comprises from 30% by weight to 40% by weight of the hydrocarbon tackifying agent.

10. The disposable absorbent article of claim 1 selected from the group consisting of a disposable diaper and an adult incontinence product.

11. The disposable absorbent article of claim 1 wherein the hot melt adhesive composition comprises:
   a. from 10% by weight to 80% by weight of a single-site catalyzed propylene based polymer and,
   from 15% by weight to 60% by weight of a high softening point hydrocarbon tackifying agent having a softening point of from 110° C. to 150° C.

* * * * *